(12) United States Patent
Calcoen et al.

(10) Patent No.: US 9,329,142 B2
(45) Date of Patent: May 3, 2016

(54) OBJECT IMAGING ASSEMBLY

(71) Applicants: Johan Calcoen, Lueven (BE); Thomas van de Laak, Kranenburg (DE)

(72) Inventors: Johan Calcoen, Lueven (BE); Thomas van de Laak, Kranenburg (DE)

(73) Assignee: KEY TECHNOLOGY, INC., Walla Walla, WA (US)

( * ) Notice: Subject to any disclaimer, the term of this patent is extended or adjusted under 35 U.S.C. 154(b) by 267 days.

(21) Appl. No.: 14/101,667

(22) Filed: Dec. 10, 2013

(65) Prior Publication Data

US 2015/0160139 A1   Jun. 11, 2015

(51) Int. Cl.
*G01N 21/85* (2006.01)
*G01N 23/20* (2006.01)
*B07C 5/342* (2006.01)

(52) U.S. Cl.
CPC ............ *G01N 23/20* (2013.01); *B07C 5/342* (2013.01); *G01N 21/85* (2013.01)

(58) Field of Classification Search
None
See application file for complete search history.

(56) References Cited

U.S. PATENT DOCUMENTS

| | | | | |
|---|---|---|---|---|
| 3,932,042 A * | 1/1976 | Faani | ............... | G01N 21/9036 209/524 |
| 6,369,882 B1 * | 4/2002 | Bruner | ............... | B07C 5/342 209/577 |
| 8,355,581 B2 * | 1/2013 | Noy | ............... | G01B 11/24 250/559.06 |
| 2002/0008055 A1 * | 1/2002 | Campbell | ............... | B07C 5/3422 209/577 |
| 2008/0174771 A1 | 7/2008 | Yan et al. | | |
| 2009/0257555 A1 * | 10/2009 | Chalmers | ............... | G01N 23/20 378/57 |
| 2010/0026807 A1 * | 2/2010 | S ther | ............... | G01N 21/8806 348/150 |
| 2012/0074047 A1 * | 3/2012 | Deefholts | ............... | B07C 5/342 209/587 |
| 2012/0138514 A1 * | 6/2012 | Janssens | ............... | G01N 21/21 209/577 |
| 2012/0200849 A1 * | 8/2012 | Balducci | ............... | G01N 21/8806 356/240.1 |
| 2012/0263275 A1 * | 10/2012 | Harding | ............... | G01N 23/20 378/71 |
| 2013/0008837 A1 * | 1/2013 | Calcoen | ............... | B07C 5/342 209/644 |
| 2013/0044207 A1 * | 2/2013 | Calcoen | ............... | B07C 5/342 348/91 |
| 2013/0229510 A1 * | 9/2013 | Killmann | ............... | B07C 5/3416 348/91 |

OTHER PUBLICATIONS

PCT Search Report dated Apr. 13, 2015.

* cited by examiner

*Primary Examiner* — Jay Patel
*Assistant Examiner* — Reza Aghevli
(74) *Attorney, Agent, or Firm* — Randall Danskin PS

(57) ABSTRACT

An object imaging assembly includes a source of individual objects which move along a predetermined course of travel; an image capture device having a line of sight which extends across the course of travel; and an electromagnetic radiation emitter which emits electromagnetic radiation in a beam which extends transversely across the predetermined course of travel and the line of sight.

17 Claims, 2 Drawing Sheets

OBJECT IMAGING ASSEMBLY

TECHNICAL FIELD

The present invention relates to an object imaging assembly, and more specifically to an object imaging assembly which provides shadowless imaging of a stream of objects to be sorted.

BACKGROUND OF THE INVENTION

The prior art is replete with numerous examples of sorting devices of various designs, and which are utilized to transport a supply of objects to be sorted along a course of travel and into an inspection station; form an image of the objects in the inspection station; determine the characteristics of the objects of interest in the inspection station by reviewing the image of the objects; identify unacceptable or foreign objects in the inspection station; transmit a sorting signal to a rejection station positioned downstream from the inspection station; and remove the unacceptable or foreign objects from the product stream which has passed through the inspection station.

Various arrangements and schemes have been developed, over time, to inspect all the surface areas of an object passing through an inspection station. Such prior art devices have included arrangements for imaging the objects passing through the inspection station from both above and below or on opposite sides of the object as the objects pass through the inspection station, or, releasing the respective objects traveling in the product stream so that they individually pass, unsupported, across a gap or move under the influence of gravity into free fall while an image of the object is taken from one or both sides of the object.

While these prior art designs have worked with varying degrees of success, many shortcomings have detracted from their usefulness. One of the chief shortcomings associated with the practices which have been utilized, heretofore, relates to the interpretation of the resulting images which are formed, and where the shadows of the object passing through the inspection station often impairs a proper identification of defective or unacceptable objects or foreign material passing through the inspection station. Attempts to remedy this problem have remained outside the grasp of designers and fabricators of such inspection and sorting devices.

An object imaging assembly which avoids the detriments associated with the prior art practices which have been utilized, heretofore, is the subject matter of the present invention.

SUMMARY OF THE INVENTION

A first aspect of the present invention relates to an object imaging assembly which includes a source of objects which are moved along a given course of travel, and wherein the course of travel has a predetermined width dimension, and opposite first and second sides; an image capturing device which is located on one of the first or second sides of the course of travel, and wherein the image capturing device has a line of sight which extends across the course of travel of the source of objects; and an electromagnetic radiation emitter which is located on one of the first or second sides of the course of travel and which, when energized, emits a source of electromagnetic radiation which is projected transversely across the course of travel of the objects, and which is reflected, at least in part, from the respective objects as they move across the line of sight of the image capturing device, and wherein the source of the objects passing through the emitted electromagnetic radiation creates individual shadows which are formed in a location which is outside the line of sight of the image capturing device.

Still another aspect of the present invention relates to an object imaging assembly which includes a source of objects to be sorted and which individually move along a course of travel which has a given width dimension, and opposite sides; a camera which is located in spaced relation relative to the first side of the course of travel, and which further has a line of sight which extends across the course of travel of the objects to be sorted, and which is further oriented substantially perpendicular relative thereto, and wherein the camera is rendered operable, when energized, to form a multiplicity of images of the individual objects to be sorted as the respective objects to be sorted move across the line of sight of the camera; an electromagnetic radiation emitter which is located in spaced relation relative to the first side of the course of travel, and which is further disposed in an acutely angulated, and spaced relation relative to each of the course of travel of the objects to be sorted, and the line of sight of the camera, and wherein the electromagnetic radiation emitter, when energized, emits electromagnetic radiation in a predetermined beam which is oriented so as to be reflected, at least in part, from the individual objects to be sorted as the respective objects move along the course of travel, and cross the line of sight of the camera, and back along the line of sight, and in the direction of the camera, and wherein the individual objects passing through the emitted electromagnetic radiation forms individual shadows of the respective objects to be sorted on the second side of the course of travel, and wherein the individual shadows are located in spaced relation relative to the line of sight of the camera; and a background image reference which is located adjacent to the second side of the course of travel, and which is further coaxially oriented relative to the line of sight of the camera.

These and other objects of the present invention will be described in greater detail hereinafter.

BRIEF DESCRIPTION OF THE DRAWINGS

Preferred embodiments of the invention are described below with reference to the following accompanying drawings.

DETAILED DESCRIPTION OF THE PREFERRED EMBODIMENT

First Embodiment

This disclosure of the invention is submitted in furtherance of the constitutional purposes of the U.S. Patent laws "to promote the progress of science and useful arts." (Article I, Section 8).

Figure 1:
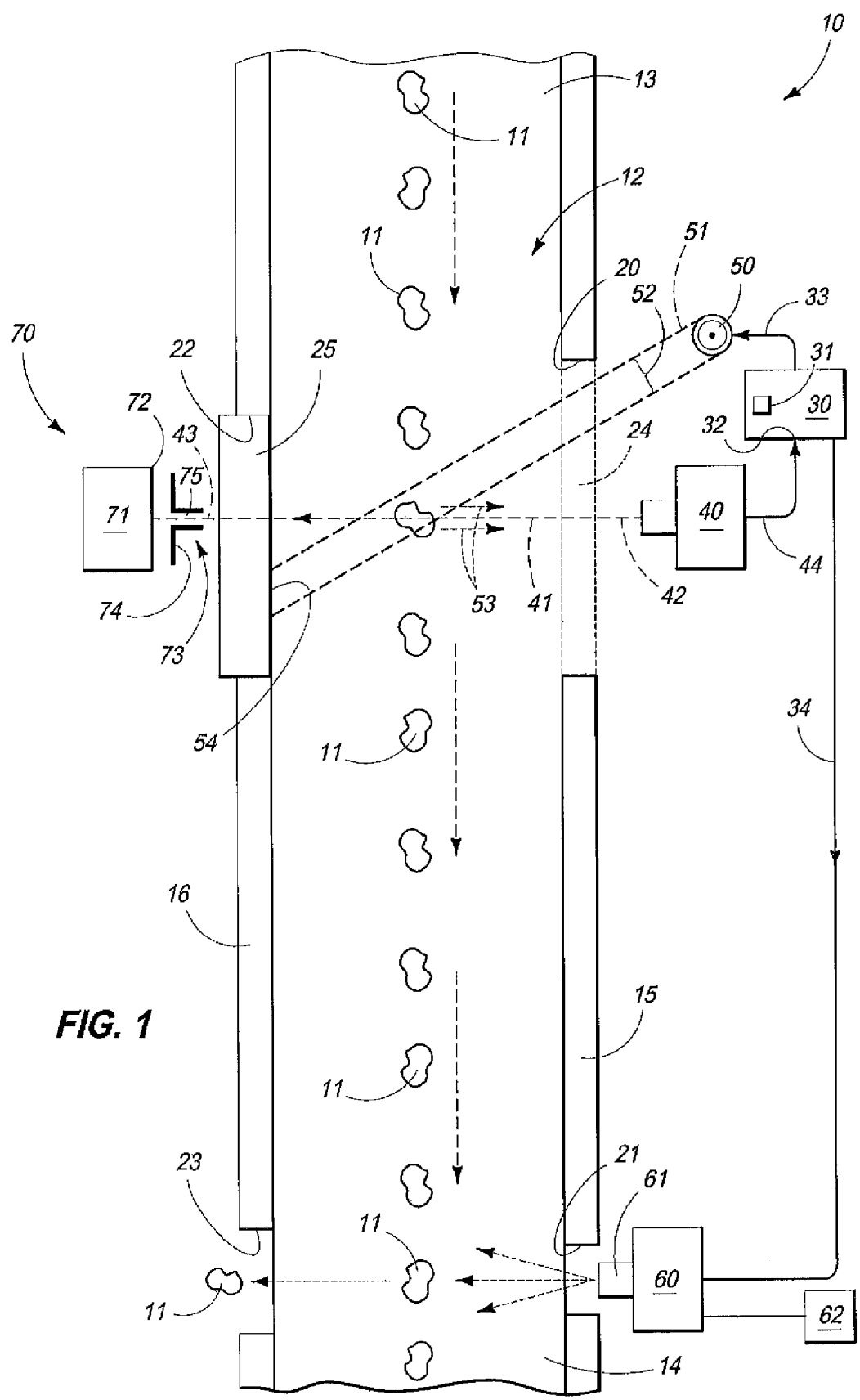
FIG. 1 is a greatly simplified, schematic, vertical sectional view of a first form of the present invention.
Figure 2:
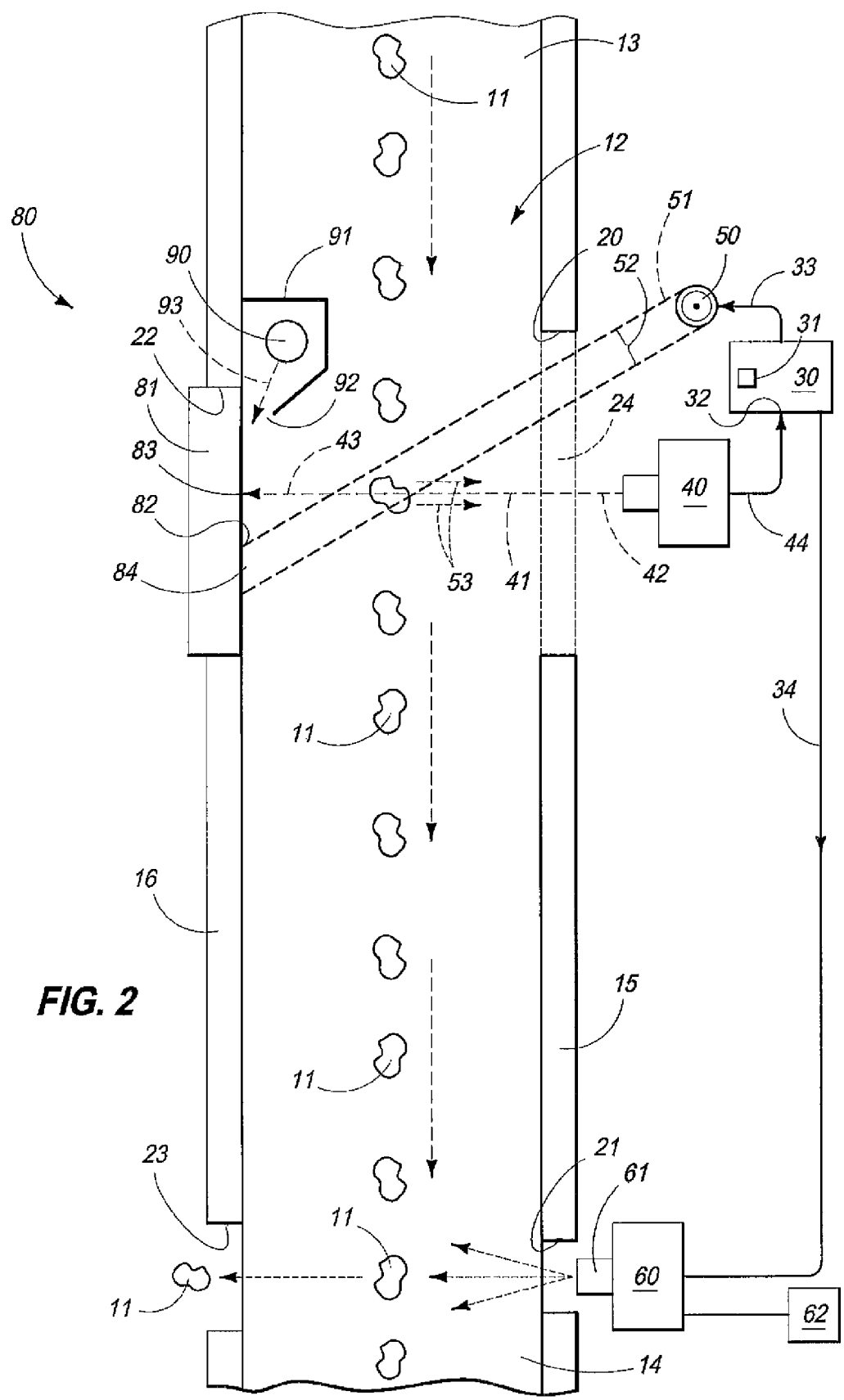
FIG. 2 is a greatly simplified, schematic, vertical sectional view of a second form of the present invention.

An object imaging assembly 10 which avoids the detriments associated with the prior art practices that have been utilized, heretofore, is best seen by references to FIGS. 1 and 2 respectively. As seen in the drawings which are provided, herewith (FIG. 1) the object imaging assembly 10 as depicted is illustrated in a simplistic manner where the objects to be sorted move downwardly under the influence of gravity. It should be understood that an embodiment of the invention can be provided and which moves a stream of objects or products vertically upwardly. Additionally, the principals of the present invention can be utilized to move objects to be sorted along a horizontal path of travel or any direction of travel, including free-fall, guided flow at a predetermined angle etc. As will be appreciated the source of objects as indicated in the drawing may have different surface topographies; color; and other predetermined characteristics which are useful in determining whether the object being sorted has desirable characteristics for use by an end user, not shown. The objects of interest may be irregular in shape have various colored exterior surfaces, or further, foreign objects or debris may have become mixed with same. Additionally, the source of the objects 11 may have a wide range of other characteristics which may be indicative of either an acceptable or unacceptable object from the perspective of an end user. As seen in FIGS. 1 and 2, the objects are only generally graphically depicted to aid in an understanding of the invention.

As seen in FIGS. 1 and 2 the source of the objects to be sorted 11 move along a course of travel 12 between a first intake end 13, and a second exhaust end 14. While the course of travel 12 is shown in the drawings as being generally vertically, downwardly, as noted, above, it is possible to make the present invention operate in an opposite direction, that is, so that the course of travel 12 can move the source of objects 11 substantially vertically upwardly. As will be appreciated, and in the arrangement as seen in FIGS. 1 and 2, the movement of the source of objects 11, generally vertically, downwardly is done under the influence of gravity. However, in the event that the invention was to be used in a manner whereby the source of objects move vertically, upwardly, such movement of the objects vertically upwardly would typically be accomplished by means of a pressurized fluid stream introduced at the intake end 14, in this alternative form of the invention (not shown). This fluid stream would typically comprise a source of air provided under pressure and which would lift or propel the objects of interest and carry them vertically upwardly along the course of travel 12 described below. Again, this same arrangement could be employed to move objects to be inspected horizontally, if that was desired.

As best seen in FIGS. 1 and 2 the course of travel 12, is defined by the first and second sides 15 and 16. The first side or sidewall further has formed therein a first and a second opening or aperture 20 and 21 respectively. Additionally, a first and second aperture 22 and 23 are individually formed in the second side 16. With regards to the apertures 20 and 21 which are formed in the first side or sidewall 15, a transparent substrate or window 24 is provided and which substantially occludes the first opening, or aperture 20, and further allows a camera, as will be described, hereinafter, to optically view or image through the aperture 20, and into the course of travel 12. The operation of the camera and other features of the invention will be discussed, below. As will be appreciated, this first transparent substrate or window 24 may be optionally removed depending upon the source of objects 11 which are being transported and sorted. Additionally, the transparent substrate or window 24 prevents dust or other debris from being deposited on or about the camera as will be discussed in greater detail hereinafter. Moreover, and as will be seen in the first embodiment of the invention as depicted in FIG. 1, a second, at least partially transparent substrate or window 25 is positioned in occluding relation relative to the first opening or aperture 22 and which is formed in the second sidewall 16. Again, this second at least partially transparent substrate 25 protects or otherwise prevents the deposit or ejection of debris, dust and other particulate material from the course of travel 12, and that might have been introduced or carried along with the source of objects 11. The at least partially transparent substrate 25 prevents this dust or debris from becoming deposited on a background image reference and which will be discussed in greater detail, below. As seen in FIG. 1 for example, the second opening 21, which is formed in the first sidewall 15 allows for an ejection assembly, as will be discussed, below, to be operably aligned relative thereto. The ejection assembly is used to remove selective objects 11 from the object stream traveling along the course of travel 12, and which have given characteristics. Furthermore, the second opening 23 which is formed in the second sidewall 16 allows ejected objects to be readily and effectively removed from the course of travel 12.

The respective embodiments of the object imaging devices, as seen in FIGS. 1 and 2, respectively, include a controller 30, which is generally known in the art. Controllers of conventional design typically include a memory 31. The memory 31 stores, in a given data structure (not shown), various acceptable and unacceptable characteristics which are visually discernible on the respective objects 11 which are to be inspected and sorted. The controller 30, including the memory 31, has an electrical input 32 which is coupled in signal receiving relation relative to a camera, and which will be discussed in greater detail, hereinafter. Still further the controller has a first electrical output 33 which is coupled in controlling relation relative to an electromagnetic radiation emitter, which, when energized, emits electromagnetic radiation of a given wave length and which is projected or otherwise passes through the first opening 20, and which is formed in the first sidewall 14, and across the course of travel 12, as will be discussed, below. Additionally, and based upon an electrical signal which is received from an image capturing device, or camera, as will be discussed, below, the controller 30 is operable to transmit an electrical sorting signal which is generally indicated by the numeral 34 to an ejector assembly of conventional design and which will be discussed, below. The ejector assembly is supplied with a source of pressurized fluid, such as air, and is effective, when rendered operable, to remove selective or individual objects from the source of objects 11 traveling along the course of travel 12. This results in a substantially sorted and uniform stream of objects 11. The operation of the controller 30, and the other assemblies mentioned, above, will also be discussed in the paragraphs which follow.

In the two embodiments of the invention as seen in the drawings, the object imaging assembly 10 includes an image capturing device or camera, and which is generally indicated by the numeral 40. While only one image capturing device is shown it will be appreciated, and understood that the present invention could employ multiple image capturing devices or cameras. Additionally the image capture device may be, in one possible form the invention, a combined laser scanner, and camera combination, not shown. The image capturing device or camera 40 is located in spaced relation relative to one of the first or second sidewalls 15 or 16 respectively, and outside the course of travel 12. The image capturing device or camera 40 has a line of sight 41 which extends transversely and substantially perpendicularly across the course of travel 12, and through which the source of objects 11 travel. The line of sight 41 has a first end 42 which begins at the image capturing device 40, and an opposite, second end 43, which terminates at a background image reference, and which will be discussed in greater detail, below. The image capturing device 40, when energized, creates a multiplicity of images of the individual objects 11 to be sorted, and which move across the line of sight 41 of the image capturing device 40. These multiplicities of images are formed into a suitable electrical signal 44 which is then provided to the controller 30 by means of the electrical input 32. As seen in the drawings, an electromagnetic radiation emitter of traditional design, 50, is located in spaced relation relative to the first sidewall 15 of the course of travel 12. The electromagnetic radiation emitter 50 is further disposed in a position so that it may emit, when energized, an acutely angulated beam of collimated electromagnetic radiation which is projected across the line of sight 41. The electromagnetic radiation emitter is further located in spaced relationship relative to each of the course of travel 12 of the objects 11 to be sorted, and the line of sight 41 of the camera or image capturing device 40. The electromagnetic radiation emitter 50, when energized, emits electromagnetic radiation 51 in a predetermined collimated beam 52 which is oriented so as to be reflected 53, at least in part, from the objects 11 to be sorted, and back in the direction of the image capturing device 40 as the objects 11 move along the course of travel 12, and across the line of sight 41. The reflected electromagnetic radiation 53 is oriented in a direction back towards, or in the direction of the imaging capturing device or camera 40 such that the camera or image capturing device 40 can form resulting images into a suitable electrical signal 44 which is supplied to the controller 30. The emitted electromagnetic radiation 51 which is not reflected from the respective objects 11, to be sorted, may be reflected in assorted different directions or reach the opposite sidewall 16. As will be appreciated, the movement of the respective objects across the emitted electromagnetic radiation 52 causes a shadow 54 to be formed on the second sidewall 16 or a region of the at least partially transparent substrate 25. The individual shadows 54 are located in spaced relationship relative to the line of sight 41 of the image capturing device or camera 40. As seen in FIGS. 1 and 2 an ejector assembly 60, of conventional design is controlled by and coupled in signal receiving relation relative to the controller 30. The ejector assembly 60 has at least one nozzle 61 which is located in fluid releasing, and force transmitting relation relative to the individual objects 11 which are traveling along the course of travel 12. The ejector assembly 60 is located downstream relative to the line of sight 41 of the image capturing assembly 40. As should be understood, a sorting signal 34, which is generated, and provided by the controller 30, is effective to cause a timely release of a pressurized source of fluid 62 through the nozzle 61 so as to cause the forcible removal of selected objects 11 which are traveling along the course of travel 12, and which have predetermined characteristics as determined by the controller 30.

The first embodiment of the invention 10 as seen in FIG. 1 includes a background image reference, which is generally indicated by the numeral 70, and which is located on the second side 16. The background image reference is located adjacent to the second transparent substrate 25, and through which the line of sight 41 extends. The background image reference 70 has a main body 71, which has a black colored exterior facing surface 72, and which absorbs a large percentage of visible electromagnetic radiation, which may be directed onto the exterior facing surface 72. Located between the main body 71, and the second transparent substrate 25 is a light trap or other assembly having highly light absorbing properties, 73. Again the light trap has an exterior facing surface 74 which is black in color, or which absorbs a large percentage of the visible electromagnetic radiation, which strikes this surface. Further, a passageway 75 is formed through the light trap 73. The line of sight 41 of the image capturing device 40, extends through the transparent substrate 25 and through the passageway 75, which is defined by the light trap 73. This arrangement allows the image capturing device 40 to see a substantially uniform black background so as to provide a contrast to the illuminated objects 11, which are individually passing through the line of sight 41, and which are further being illuminated by the collimated beam 52 of the electromagnetic radiation 51, and which is being emitted by the energized electromagnetic radiation emitter 50. Further, if the form of the invention, as employed utilizes multiple image capturing devices 40, it will be understood that the multiple image capturing devices could each conceivably utilize the same background image reference 70.

Second Embodiment

The second embodiment of the invention is generally indicated by the numeral 80 in FIG. 2. In describing this embodiment of the invention, it should be understood that similar structures bear similar numerals in the second embodiment of the invention. A further discussion regarding the structures which are common in each of the first and second embodiments of the invention is therefore not warranted. With regards to the second form of the invention 80, the present invention includes an opaque background image reference or reflector, which is generally indicated by the numeral 81, and which is further positioned in a substantially occluding relationship relative to the first opening 22, and which is further formed in the second side or sidewall 16, as seen in FIG. 2. The background image reference 81, as noted, is substantially opaque, and has a given surface color. The surface color is selected so as to reflect emitted electromagnetic radiation, which strikes the interior facing surface 82 thereof. As seen in FIG. 2, the line of sight 41 of the camera or imaging apparatus 40 intersects the interior facing surface 82, at a point of intersection 83. Still further, as seen in FIG. 2, the emitted electromagnetic radiation 51, which has been formed into a collimated beam 52 by the energizing of the electromagnetic radiation emitter 50, is directed transversely, and acutely angularly across the path of travel 12. As will be recognized, as the individual objects 11 pass through the beam of electromagnetic radiation 52, the individual objects 11 cast or otherwise form a shadow 84, which is formed on a region of the interior facing surface 82, which is disposed in spaced relation relative to the point of intersection 83, and where the line of sight 41 intersects the interior facing surface of the background image reference 81. As seen in FIG. 2, and in the second form of the invention 80, a second electromagnetic radiation emitter 90 is provided, and which is located within the course of travel 12. The second electromagnetic radiation emitter 90 is enclosed within and protected by a housing 91. The housing 91 has an aperture 92 formed therein, and which allows the release of emitted electromagnetic radiation 92, which is provided or generated by the second electromagnetic radiation emitter 91, when it is energized. The emitted electromagnetic radiation 93 is directed by the aperture 92 onto the interior facing surface 82 of the opaque background image reference 81. The electromagnetic radiation or light, as provided, is scattered across the interior facing surface 82 in order to provide a uniformly colored background reference that may be seen along the line of sight 41 of the camera 40. Again, when forming an image, shadows which are generated or cast by the individual objects 11 which are passing through the emitted electromagnetic radiation 51 are cast onto a region 84, which is remote from the point of intersection 83 of the line of sight 41 with the illuminated background image reference 81. In this manner, objects passing along the path of travel 12, and across the line of sight 41, are uniformly illuminated and are seen against a uniformly illuminated opaque background image reference reflector 81. The imaging which subsequently takes place by the operation of the camera 40, and the resulting images produced, are without any shadows or other distortions that might be occasioned by a shadow being cast by the object being imaged onto the opaque background image reference 81.

As earlier discussed, such images formed or generated by the camera 40 are provided to the controller 30, which has a memory 31, and which then subsequently determines whether the generated images, as provided by the camera 40, disputes objects having predetermined undesirable characteristics. If undesirable characteristics are detected, an electrical signal 34 is provided, and which is then supplied to the ejector assembly 60. The electrical signal 34, subsequently causes the ejector assembly 60 to timely release a source of a fluid, under pressure 62, and through the nozzle 61, so as to selectively and forcibly engage a predetermined object 11 which is passing thereby. This is effective in causing the rejected object 11 to be moved out of the course of travel 12, and pass through the second opening 23, which is defined by the second side or sidewall 16.

Operation

The operation of the described embodiments of the present invention are believed to be readily apparent and are briefly summarized at this point.

A first aspect of the present invention 10 relates to an object imaging assembly 10, which includes a source of individual objects 11, which are moved along a given course of travel 12, and wherein the course of travel 12 has a predetermined width dimension, and opposite first and second sides 15 and 16, respectively. The object imaging assembly 10 further includes an image capturing device 40, which is located on one of the first or second sides 15 and 16, respectively, of the course of travel 12, and wherein the image capturing device 40 has a line of sight 41, which extends transversely across the course of travel 12 of the source of objects 11. The object imaging assembly 10 further includes an electromagnetic radiation emitter 50, which is located in one of the first or second sides 15 and 16, respectively, of the course of travel 12, and which, when energized, emits a source of electromagnetic radiation 51, which is projected across the course of travel 12 of the objects 11, and which is further reflected, at least in part, from the respective objects 11 as they move across the line of sight 41 of the image capturing device 40, and wherein the source of the individual objects passing through the emitted electromagnetic radiation 51 creates individual shadows 54, which are formed in a location which is outside the line of sight 41 of the image capturing device 40.

As disclosed in the drawings, and in the specification, the image capturing device 40 captures electromagnetic radiation 51, which is reflected from the respective objects 11, and which pass across the line of sight 41 of the image capturing device and forms the resulting image 44. In the arrangement as seen in the drawings, the electromagnetic radiation emitter 50 is located on the same side of the course of travel 12 as the image capturing device 40. Still further, and while studying the drawings, it will be seen that the electromagnetic radiation emitter 50 emits electromagnetic radiation 51, which is formed into a resulting collimated beam 52 of electromagnetic radiation. In the arrangement as disclosed in the specification, the object imaging assembly 10 further includes a background image reference 70/81 and which is located along the line of sight 41 of the image capturing device 40, and is further positioned on the opposite side 16 of the course of travel 12 relative to the imaging capturing device 40. As seen in the drawings, the location where the individual shadows 54/84 are formed, have locations which are disposed in spaced relation relative to the background image reference 70/81. As seen in the first form of the invention 10, as illustrated in FIG. 1, the background image reference 70 is black in color or has another coating which absorbs a large percentage of visually discernible electromagnetic radiation, and is further not directly illuminated. In the second embodiment of the invention 80, the background image reference 81 has a given color (not black or highly light absorbing), and is additionally directly illuminated by a second electromagnetic radiation emitter 90. In the two forms of the invention which are disclosed, a transparent window 24 is provided and which is located along the line of sight 41 of the image capturing device 40. In the arrangement as seen in the drawings, the beam of electromagnetic radiation 52 is oriented in an acutely angulated relationship relative to each of the course of travel 12, of the objects 11, and the line of sight 41 of the image capturing device 40.

As will be appreciated by a study of the drawings, the object imaging assembly 10 is arranged such that the course of travel 12 of the individual objects 11 is substantially vertically oriented. In one possible form of the invention, the objects 11 move vertically downwardly along the course of travel 12, and under the influence of gravity. In another possible form of the invention, not shown, the objects 11 move vertically upwardly along the course of travel 12 by means of an injected fluid stream [not shown]. In still another possible form of the invention, the objects to be sorted 11 move horizontally along the course of travel 12, again, not shown. In the various forms of the invention as illustrated, the line of sight 41 of the image capturing device 40 is substantially perpendicularly oriented relative to the course of travel 12.

Therefore, it will be seen that the present assembly provides a convenient means for effectively image objects traveling along a course of travel, and which are to be sorted in such a fashion so as to provide resulting, substantially shadowless images. The ability to produce a shadowless images increases the contrast of the resulting images, and the ability for an imaging apparatus or camera to detect abnormalities or other defects in an object to be sorted, This provides a convenient means for generating accurate sorting signals for use with a downstream workstation which utilizes an ejector assembly to remove defective products or other contaminants from an object stream, and thus provides a resulting substantially uniformly sorted, and homogeneous product for use in further downstream processes.

In compliance with the statutes, the invention as has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms and modifications within the proper scope of the appended claims properly interpreted in accordance with the Doctrine of Equivalence.

The invention claimed is:
1. An object imaging assembly comprising:
a source of individual objects which are moved along a given course of travel, and wherein the course of travel has a predetermined width dimension, and opposite first and second sides;
an image capturing device which is located on one of the first or second sides of the course of travel, and wherein the image capturing device has a line of sight which extends transversely across the course of travel of the source of objects;
a background image reference which is located along the line of sight of the image capturing device, and which is positioned on the opposite side of the course travel relative to the image capturing device; and a first electromagnetic radiation emitter which is located on one of the first or second sides of the course of travel and which, when energized, emits a source of electromagnetic radiation which is projected across the course of travel of the objects, and which is reflected, at least in part, from the respective objects as they move across the line of sight of the image capturing device, and wherein the source of objects passing through the emitted electromagnetic radiation creates individual shadows which are formed in a location which is spatially separated from, and outside the line of sight of the image capturing device, and wherein the background image reference has a given color, and is directly illuminated by a second electromagnetic radiation emitter.

2. An object imaging assembly as claimed in claim 1, and wherein the image capturing device captures electromagnetic radiation which is reflected from the respective objects which pass across the line of sight of the image capturing device, and forms a resulting image.

3. An object imaging assembly as claimed in claim 1, and wherein the first electromagnetic radiation emitter is located on the same side of the course of travel as the image capturing device.

4. An object aging device as claimed in claim 1, and wherein the first electromagnetic radiation emitter emits electromagnetic radiation which is formed into a resulting collimated beam of electromagnetic radiation.

5. An object imaging assembly as claimed in claim 1, and wherein the background image reference is black in color, and is not directly illuminated by the second electromagnetic radiation emitter.

6. An object imaging assembly as claimed in claim 1, and wherein a transparent window is provided and which is located along the line of sight of the image capturing device, and between the course of travel of the objects and the background image reference.

7. An object imaging assembly as claimed in claim 4, and wherein the beam of emitted electromagnetic radiation is oriented in an acutely angulated relationship relative to each of the course of travel of the objects, and the line of sight of the image capturing device.

8. An object imaging assembly as claimed in claim 1, and wherein the course of travel of the individual objects is substantially vertically oriented.

9. An object imaging assembly as claimed in claim 8, and wherein the objects move vertically downwardly along the course of travel, and under the influence of gravity.

10. An object imaging assembly as claimed in claim 8, and wherein the objects move vertically upwardly along the course of travel by means of a fluid stream.

11. An object imaging assembly as claimed in claim 8, and wherein the objects move horizontally along the course of travel.

12. An object imaging assembly as claimed in claim 7, and wherein the line of sight of the image capturing device is substantially perpendicular relative to the course of travel.

13. An object imaging assembly, comprising:

a source of objects to be sorted and which individually move along a predetermined course of travel which has a given width dimension, and opposite sides, and wherein the course of travel has a first intake end, and a second, exhaust end;

a camera which is located in spaced relation relative to the first side of the course of travel, and which further has a line of sight which extends across the course of travel of the objects to be sorted, and which is further oriented substantially perpendicular relative thereto, and wherein the camera is rendered operable, when energized, to form a multiplicity of images of the individual objects to be sorted as the respective objects to be sorted move across the line of sight of the camera;

an electromagnetic radiation emitter which is located in spaced relation relative to the first side of the course of travel, and which is further disposed in an acutely angulated, and spaced relationship relative to each of the course of travel of the objects to be sorted, and the line of sight of the camera, and wherein the electromagnetic radiation emitter, when energized, emits electromagnetic radiation in a predetermined beam which is oriented so as to be reflected, at least in part, from the individual objects to be sorted as the respective objects move along the course of travel, and cross the line of sight of the camera, and back along the line of sight, and in the direction of the camera, and wherein the individual objects passing through the emitted electromagnetic radiation forms individual shadows of the respective objects to be sorted on the second side of the course of travel, and wherein the individual shadows are spatially, separated relative to the line of sight of the camera;

an ejection assembly which is located downstream of the line of sight of the camera, and upstream relative to the second, exhaust end of the course of travel;

a controller which is coupled in image receiving, and controlling relation relative to the camera; the electromagnetic radiation emitter; and the ejection assembly; and a background image reference which is located adjacent to the second side of the course of travel, and which is further coaxially oriented relative to the line of sight of the camera, and wherein the objects to be sorted have a plurality of predetermined characteristics, and wherein the controller receives the individual images formed by the camera, and then forms and transmits a sorting signal based upon the predetermined characteristics of the objects which are to be sorted, and which are identified in the images that are received, and wherein the controller transmits the sorting signal to the ejection assembly, and which operates to remove objects having a predeterminded characteristic, and which are moving along the course of travel, and which have passed through the line of sight of the camera.

14. An object imaging device as claimed in claim 13, and wherein the background image reference has a black color, and is not directly illuminated by the electromagnetic radiation emitter.

15. An object imaging assembly as claimed in claim 13, and wherein the background image reference has a given color, and is directly illuminated by a second electromagnetic radiation emitter.

16. An object imaging assembly as claimed in claim 15, and wherein the respective electromagnetic radiation emitters emit discreet predetermined bands of electromagnetic radiation which have different wavelengths.

17. An object imaging assembly as claimed in claim 13, and wherein the emitted electromagnetic radiation is collimated, at least in part.

* * * * *